(12) United States Patent
Seifert et al.

(10) Patent No.: US 6,384,239 B1
(45) Date of Patent: May 7, 2002

(54) METHOD FOR PRODUCING MONOHALOGENATED 2-OXO-1,3-DIOXOLANES

(75) Inventors: Bernhard Seifert, Ober-Ramstadt; Sylvia Becker, Seeheim-Jugenheim, both of (DE)

(73) Assignee: Merck Patent Gesellschaft mit beschrankter Haftung, Darmstadt (DE)

( * ) Notice: Subject to any disclaimer, the term of this patent is extended or adjusted under 35 U.S.C. 154(b) by 0 days.

(21) Appl. No.: 09/830,926

(22) PCT Filed: Oct. 27, 1999

(86) PCT No.: PCT/EP99/08113

§ 371 Date: May 3, 2001

§ 102(e) Date: May 3, 2001

(87) PCT Pub. No.: WO00/27837

PCT Pub. Date: May 18, 2000

(30) Foreign Application Priority Data

Nov. 5, 1998 (DE) .......................... 198 50 906

(51) Int. Cl.$^7$ ........................................... C07D 317/42
(52) U.S. Cl. .................... 549/229; 204/157.69
(58) Field of Search ...................... 549/229; 204/157.69

(56) References Cited

U.S. PATENT DOCUMENTS 2,918,478 A  12/1959  Newman
3,021,340 A  *  2/1962  Anderson et al. ........... 549/229

FOREIGN PATENT DOCUMENTS

DE   1203796    10/1959
JP   11171882   6/1999

OTHER PUBLICATIONS

Chem. Abstracts, vol. 131, No. 5, 1999, abstract number 58816k & JP 11171882 (Jun. 29, 1999).

* cited by examiner

Primary Examiner—Floyd D. Higel
Assistant Examiner—Kamal Saeed
(74) Attorney, Agent, or Firm—Millen, White, Zelano & Branigan, P.C.

(57) ABSTRACT

The invention relates to a process for the preparation of monohalogenated 2-oxo-1,3-dioxolanes of the general formula $$C_3H_3XO_3 \qquad (I)$$

in which
  X is Cl or Br,
characterized in that the monohalogenation is carried out starting from ethylene carbonate with sulfuryl dihalides under UV irradiation and in the absence of solvents.

13 Claims, No Drawings

METHOD FOR PRODUCING MONOHALOGENATED 2-OXO-1,3-DIOXOLANES

The present invention relates to a process for the preparation of monohalogenated 2-oxo-1,3-dioxolanes of the general formula $$C_3H_3XO_3 \tag{I}$$

in which

X is Cl or Br, characterized in that the monohalogenation is carried out starting from ethylene carbonate with sulfuryl dihalides under UV irradiation and in the absence of solvents.

Halogenated 2-oxo-1,3-dioxolanes are added to the solvents in electrochemical cells. They are used to increase the stability of the electrode materials. In addition, they are intermediates for the preparation of vinylene carbonate (II) which is used as an additive in electrolyte solutions for electrochemical cells. The vinylene carbonate acts as a stabilizer for the electrode materials. Vinylene carbonates are obtained by means of an elimination reaction from the monohalogenated 2-oxo-1,3-dioxolanes (I) or else by means of the reaction of dihalogenated compounds (III) with Zn, as described by M. S. Newman in J. Am. Chem. Soc., 77, 3789–3793, (1955).

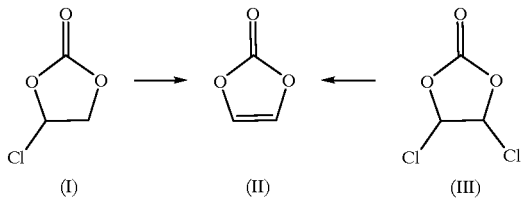

Chlorinated 2-oxo-1,3-dioxolanes such as 4-chloro-2-oxo-1,3-dioxolane (I) are usually synthesized by chlorination of the corresponding 2-oxo-1,3-dioxolanes (IV). In U.S. Pat. No. 3,021,340, ethylene carbonate (2-oxo-1,3-dioxolane) is heated to boiling point in tetrachloromethane and anhydrous iron chloride. Chlorine is passed through the solution for 36 hours. Distillative work-up gives a mixture of mono-and dichlorinated dioxolane (I) and (III).

The change in the reaction conditions, such as, for example, irradiation of the reaction solution with a 350 W lamp, leads to a significant shortening of the reaction time (R. G. Finke et al., J. Am. Chem. Soc. (105), 7592–7604, (1983)). In this process too, 4,5-dichloro-2-oxo-1,3-dioxolane (III) is formed in addition to 4-chloro-2-oxo-1,3-dioxolane (I).

The chlorination can be carried out not only using chlorine by irradiation with light at a suitable wavelength, but also using substances which decompose to form free radicals. It has been observed that when sulfuryl chloride is used as the chlorinating agent, small amounts of organic peroxides have activating properties similar to light (M. S. Kharasch et al., Am. Soc., (61), 2142, (1939); (62), 925 ff., (1940)). In G. Wulff et al., Chem. Ber. (125), 473–477, (1992), sulfuryl chloride is used for the synthesis of chlorinated 2-oxo-1,3-dioxolanes. The solution is heated in tetrachloromethane and irradiated with a 500 W lamp. The monochlorinated dioxolane and the dichlorinated dioxolane are isolated.

The use of tetrachloromethane as solvent requires increased safety precautions since this compound is classified as toxic, injurious to health, causing irreversible damage, and harmful to the environment.

The object of the invention was therefore to develop an environmentally friendly and cost-effective process for selectively synthesizing the monochlorinated compound.

The object according to the invention is achieved by a novel process for the preparation of monohalogenated 2-oxo-1,3-dioxolanes of the general formula $$C_3H_3XO_3 \tag{I}$$

in which

X is Cl or Br, characterized in that the monohalogenation is carried out starting from ethylene carbonate with sulfuryl dihalides under UV irradiation at temperatures between 0° C. and 90° C. in the absence of solvents, under atmospheric pressure and in the presence of atmospheric oxygen or optionally under a protective-gas atmosphere.

Experiments have shown that the reaction of the starting compound 2-oxo-1,3-dioxolane (IV) with sulfuryl chloride can be carried out without tetrachloromethane.

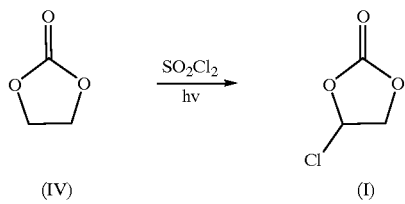

The rate of the reaction proved to be only slightly lower than for the synthesis with tetrachloromethane ($CCl_4$). Surprisingly, it has been found that when equimolar amounts of ethylene carbonate and sulfuryl chloride are used in the process according to the invention, the formation of the undesired dichlorinated by-product is avoided if the process is carried out in the absence of tetrachloromethane.

Additionally, work-up is simplified since neither the solvent nor dichloroethylene carbonate have to be removed by distillation. In the case of further conversion to vinylene carbonate, it is possible to dispense completely with prior work-up since the unreacted ethylene carbonate can be removed by distillation without problem following this further reaction step.

A particular advantage of the process according to the invention is that despite the absence of the solvent, a high reaction rate and high quantitative yield are obtained. In carrying out the process according to the invention, it has also been found that the evolution of gas, i.e. the formation of HCl and $SO_2$, can be regulated by means of the radiation intensity. This makes it considerably easier to carry out the process since it is not necessary to exhaust large amounts of gas within a very short time. Because the gas is evolved considerably more slowly. It is possible to dispense with the batchwise introduction of the starting materials, and it is not necessary to wait for the evolution of gas to subside either. For scaling-up of the reaction, not only is the batchwise procedure possible, but also continuous operation. An advantage of this is the low residence time because of the high rate of reaction. The reaction can be carried out continuously, for example through a cascade of two or more conventional photochemical reactors or thin-film roll photochemical reactors. Because tetrachloromethane is dispensed with as solvent, the authorization procedure for a large-scale industrial plant is considerably simplified. Contrary to implementation procedures to date, the reaction does not have to be carried out under a protective-gas atmosphere. The saving in terms of raw materials, e.g. of solvent and of the protective gas, and the consequently considerably simplified apparatus lead to considerably reduced costs.

For the preparation of monohalogenated 2-oxo-1,3-dioxolanes, a coolable apparatus fitted with appropriate equipment for monitoring the temperature in the reaction vessel, a gas inlet and outlet line, a mixing device, and equipment for generating UV radiation, such as, for example, a high-pressure mercury vapour lamp, is required. The apparatus can be connected upstream of gas-scrubbing equipment, for the absorption of HCl and $SO_2$.

To carry out the process according to the invention, ethylene carbonate and sulfuryl dihalides are introduced into the apparatus and exposed under a pressure which is atmospheric or slightly above atmospheric and in the presence of atmospheric oxygen or optionally under a protective-gas atmosphere. The temperature in the reaction vessel is maintained at between 0° C. and 70° C. by means of iced-water cooling or a cryostat or the like. The reaction kinetics are good at temperatures between 20° C. and 70° C. The exposure time is variable and is between 15 and 300 min, depending on the intensity of the radiation and the desired conversion. For a batchwise addition of the sulfuryl chloride and an exposure time of 30 min, a yield of monohalogenated 2-oxo-1,3-dioxolane of 79% was achieved. A continuous, equimolar metered addition of sulfuryl halide offers the advantage that the gas is evolved in a controllable manner. The exposure time can thus be reduced to from 15 to 60 min. It is therefore possible for the person skilled in the art to choose, analogous to the amounts of starting materials used, the corresponding parameters such as temperature and exposure time so that they are optimal. Surprisingly, when the reaction was carried out using equimolar amounts, no traces of a dihalogenated by-product were found. Distillative work-up is simplified since only unreacted starting material has to be removed, and not by-products and solvent.

The examples given below are given to illustrate the present invention more clearly, but are not intended to limit the invention to the features disclosed therein.

EXAMPLES

Example 1

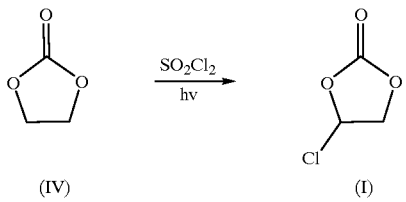

80 g of ethylene carbonate and 73.6 ml of sulfuryl chloride are introduced, with stirring, into a coolable apparatus fitted with high-pressure mercury vapour lamp, thermometer, stirrer, gas inlet and outlet line and downstream gas-scrubbing bottles containing aqueous sodium hydroxide solution. The process is not carried out under a protective-gas atmosphere. The photolytic decomposition of sulfuryl chloride is started by switching on the high-pressure mercury vapour lamp. The reaction solution is maintained at a temperature between 20° C. and 40° C. by means of water-cooling. After an exposure time of 15, 30 and 60 min, samples are taken for kinetic analysis. The results are given in Table 1.

TABLE 1

Photolytic reaction of ethylene carbonate with sulfuryl chloride without solvent

| Exposure time [min] | Conversion [%] | Chloroethylene carbonate: dichloroethylene carbonate ratio |
|---|---|---|
| 15 | 61 | 100:0 |
| 30 | 79 | 100:0 |
| 60 | 79 | 100:0 |

As a result of the absence of solvent and of the undesired by-product dichloroethylene carbonate, it is possible to dispense with distillative work-up.

Comparative Example 1

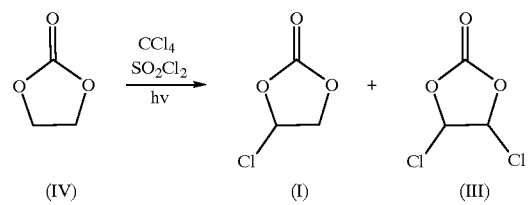

80.0 g of ethylene carbonate, 73.6 ml of sulfuryl chloride and 300 ml of tetrachloromethane are introduced, with stirring, into a coolable apparatus fitted with high-pressure mercury vapour lamp, thermometer, stirrer, gas inlet and outlet line and downstream gas-scrubbing bottles containing aqueous sodium hydroxide solution. The mixture is two-phase, the carbonate being only negligibly soluble in the $CCl_4$ phase. The photolytic decomposition of sulfuryl chloride is started by switching on the high-pressure mercury vapour lamp, which immediately triggers a vigorous evolution of gas. The reaction mixture is maintained at temperatures between 20° C. and 40° C. by means of water-cooling. After an exposure time of 15 and 60 min, samples are taken for kinetic analysis. The results are given in Table 2.

TABLE 2

Photolytic reaction of ethylene carbonate with sulfuryl chloride in tetrachloromethane

| Exposure time [min] | Conversion [%] | Chloroethylene carbonate: dichloroethylene carbonate ratio |
|---|---|---|
| 15 | 74 | 96:4 |
| 60 | 84 | 94:6 |

After the reaction mixture has cooled to room temperature, residues of $CCl_4$ are distilled off at atmospheric pressure, and the crude product is then distilled in an oil-pump vacuum of 7 torr at a transition temperature interval of from 50 to 88° C. 88.8 g of a pale yellow oil, consisting of 78% of chloroethylene carbonate, 6% of dichloroethylene carbonate and 16% of ethylene carbonate, are isolated.

What is claimed is:

1. A process for the preparation of monohalogenated 2-oxo-1,3-dioxolanes of the formula $$C_3H_3XO_3 \quad (I)$$

in which

X is Cl or Br, wherein ethylene carbonate is monohalogenated with sulfuryl dihalide under UV irradiation in the absence of solvents.

2. A process according to claim 1, wherein the ethylene carbonate is monohalogenated at temperatures between 20° C. and 70° C.

3. A process according to claim 1, wherein the ethylene carbonate is monohalogenated under a protective-gas atmosphere.

4. A process according to claim 1, wherein the ethylene carbonate is monohalogenated at temperatures between 20° C. and 40° C. by means of water-cooling.

5. A process according to claim 1, wherein the ethylene carbonate is monohalogenated at temperatures between 20° C. and 40° C. by means of a cryostat.

6. A process according to claim 1, wherein the ethylene carbonate is monohalogenated for between 15 and 300 minutes.

7. A process according to claim 1, wherein the ethylene carbonate is monohalogenated by a continuous metered addition of sulfuryl halide.

8. A process according to claim 1, wherein the ethylene carbonate is monohalogenated starting from equimolar amounts of ethylene carbonate with sulfuryl dihalides.

9. A process according to claim 1, wherein the ethylene carbonate is monohalogenated under atmospheric pressure and in the presence of atmospheric oxygen.

10. A process according to claim 1, wherein the ethylene carbonate is monohalogenated under atmospheric pressure and in the presence of a protective-gas atmosphere.

11. A process according to claim 1, wherein the ethylene carbonate is monohalogenated under slightly above atmospheric pressure and in the presence of atmospheric oxygen.

12. A process according to claim 1, wherein the ethylene carbonate is monohalogenated under slightly above atmospheric pressure and in the presence of a protective-gas atmosphere.

13. A process according to claim 1, wherein the ethylene carbonate is monohalogenated at temperatures between 0° C. and 70° C.

* * * * *